United States Patent [19]
White

[11] 3,976,574
[45] Aug. 24, 1976

[54] NEGATIVE PRESSURE CONTROL SYSTEM

[75] Inventor: Robert Lee White, Golden, Colo.

[73] Assignee: Cobe Laboratories, Inc., Lakewood, Colo.

[22] Filed: Nov. 4, 1974

[21] Appl. No.: 520,336

[52] U.S. Cl. .............................. 210/188; 210/321 A
[51] Int. Cl.² ........................................ B01D 31/00
[58] Field of Search ................. 210/90, 22, 23, 321, 210/85, 87, 433, 96, 188

[56] References Cited
UNITED STATES PATENTS

| | | | |
|---|---|---|---|
| 3,598,727 | 8/1971 | Willock | 210/321 X |
| 3,626,670 | 12/1971 | Pecker | 210/321 X |
| 3,640,388 | 2/1972 | Ferrari | 210/321 X |
| 3,756,234 | 9/1973 | Kopp | 210/321 X |
| 3,827,561 | 8/1974 | Serfass et al. | 210/321 X |
| 3,847,809 | 11/1974 | Kopf | 210/321 X |

Primary Examiner—Theodore A. Granger
Attorney, Agent, or Firm—Reising, Ethington, Barnard

[57] ABSTRACT

A dialysate flow control system is disclosed for an artificial kidney machine. The flow control system produces dialysate flow at negative pressure through the dialyzer and comprises a flow controller and first pump upstream of the dialyzer and a second pump downstream of the dialyzer. The negative pressure between the flow regulator and the first pump is utilized for deaeration and an air accumulator is disposed downstream of the first pump and provided with an air discharge path into the dialysate flow path downstream of the dialyzer. A negative pressure regulator automatically regulates the dialysate pressure in the dialyzer at a manually adjustable value and comprises regulator means responsive to the average value of negative pressure in the dialyzer to provide suction relief to the second pump as needed to maintain the selected pressure value.

10 Claims, 6 Drawing Figures

NEGATIVE PRESSURE CONTROL SYSTEM

This invention relates to artificial kidneys and more particularly it relates to a dialysate flow control system.

By hemodialysis in an artificial kidney, water and certain waste materials are removed from the blood of the patient. The process is carried out in a dialyzer which includes a flow path for the patient's blood separated by a dialyzing medium, in the form of a semipermeable membrane, from a flow path for a liquid dialysate. Most of the waste removal occurs by mass transfer through the membrane and water removal occurs by ultrafiltration through the membrane.

In artificial kidneys, the efficacy of the water and waste removal from the blood of the patient depends upon the proper control of the condition of the dialysate and the flow thereof through the dialyzer. There are several parameters of the dialysate which must be controlled, including the pressure of the dialysate and the air content of the dialysate in the dialyzer. The subject matter of this invention is a dialysate control system which controls the negative pressure of the dialysate in the dialyzer and the deaeration of the dialysate prior to its admission to the dialyzer.

Artificial kidneys of conventional design employ dialysate flow systems which deliver the dialysate to the dialyzer at a negative pressure, i.e. a pressure less than atmospheric; the patient's blood is delivered to the dialyzer, usually with the aid of an extracorporeal blood pump, at a controlled pressure, usually at a positive pressure, i.e. above atmospheric. The value of negative pressure of the dialysate has significant influence upon the ultrafiltration rate in the hemodialysis treatment. The ultrafiltration rate should be adjusted in value to meet the needs of the patient and for different patients the desired rate may vary over a wide range. For a given patient the negative pressure value should be adjusted and maintained with a high degree of accuracy.

The hemodialysis treatment must be performed without permitting any substantial quantity of air (or other gas) to be transferred to the patient's blood through the dialyzer membrane from the dialysate. The dialysate is usually prepared in the artificial kidney machine by mixing a concentrated dialysis solution with "tap" water from the municipal water supply. Tap water is pressurized and usually cool as it is delivered through the supply line to the artificial kidney; in this condition it contains a relatively large quantity of air in solution. Unless the dialysate is deaerated, the warming thereof to body temperature and reducing the pressure in the dialyzer would result in an excessive quantity of air coming out of solution in the dialyzer. Such air will tend to cross the membrane and enter the blood with the undesirable result of causing frothing of the blood in the drip chamber. It is desired, therefore, to remove the excess quantity of air from the dialysate before it is admitted to the dialyzer.

Heretofore, artifical kidneys have operated with the dialysate flowing through the dialyzer at negative pressure; however, such devices have not provided the desired degree of accuracy. Furthermore, such devices have required manual supervision, by the patient himself or an attendant, to assure maintenance of the desired negative pressure and ultrafiltration rate during the term of the hemodialysis treatment. Artificial kidneys with a negative pressure control system are disclosed in the Kylstra U.S. Pat. No. 3,212,642, Serfess et al. U.S. Pat. No. 3,441,136 and the Willock U.S. Pat. No. 3,598,727. The systems disclosed in these patents include a suction pump downstream of the dialyzer with a manually adjustable bypass valve around the pump and a pressure gauge for establishing the negative pressure in the dialyzer. Heretofore, the deaeration of the dialysate prior to admission thereof to the dialyzer has required opening of the dialysate flow path to the atmosphere, directly or indirectly, with the resultant risk of bacterial contamination. In addition to the problem of contamination, previously known deaeration systems require special devices for dumping the accumulated air to the atmosphere, such devices being complex and lacking in reliability. The Willock U.S. Pat. No. 3,598,727 discloses an artificial kidney in which the dialysate is deaerated prior to admitting the dialysate at negative pressure to the dialyzer; this system, however, dumps the accumulated air to the atmosphere by means which indirectly opens the dialysate flow path to the atmosphere.

The invention set forth herein provides an artificial kidney with a dialysate flow system in which the dialysate in the dialyzer is automatically regulated at a selected negative pressure. This is accomplished by a regulator which senses and responds to deviation of the dialysate pressure in the dialyzer from a predetermined value and controls the admission of make-up fluid, such as air, to the intake of the suction pump so as to regulate the negative pressure at the predetermined value. Furthermore, this invention provides for a very wide range of adjustment of negative pressure in the dialyzer while retaining a highly effective degassing capability, even when the dialyzer negative pressure is set for a small value of negative pressure. This is accomplished by providing a flow restricting means and two pumping stages in the flow path for the dialysate, the first pumping stage producing a flow rate in excess of the flow restricting means and the second pumping stage producing a flow rate greater than the first. Additionally, this invention provides degassing of the dialysate prior to admission to the dialyzer without opening the dialysate flow path to the atmosphere. This is achieved by subjecting the dialysate to high negative pressure and accumulating the resulting air at a lower negative pressure point in the flow path and discharging the air into the flow path at a higher negative pressure downstream of the dialyzer. A more complete understanding of this invention may be obtained from the detailed description that follows, taken with the accompanying drawings in which:

Figure 1:
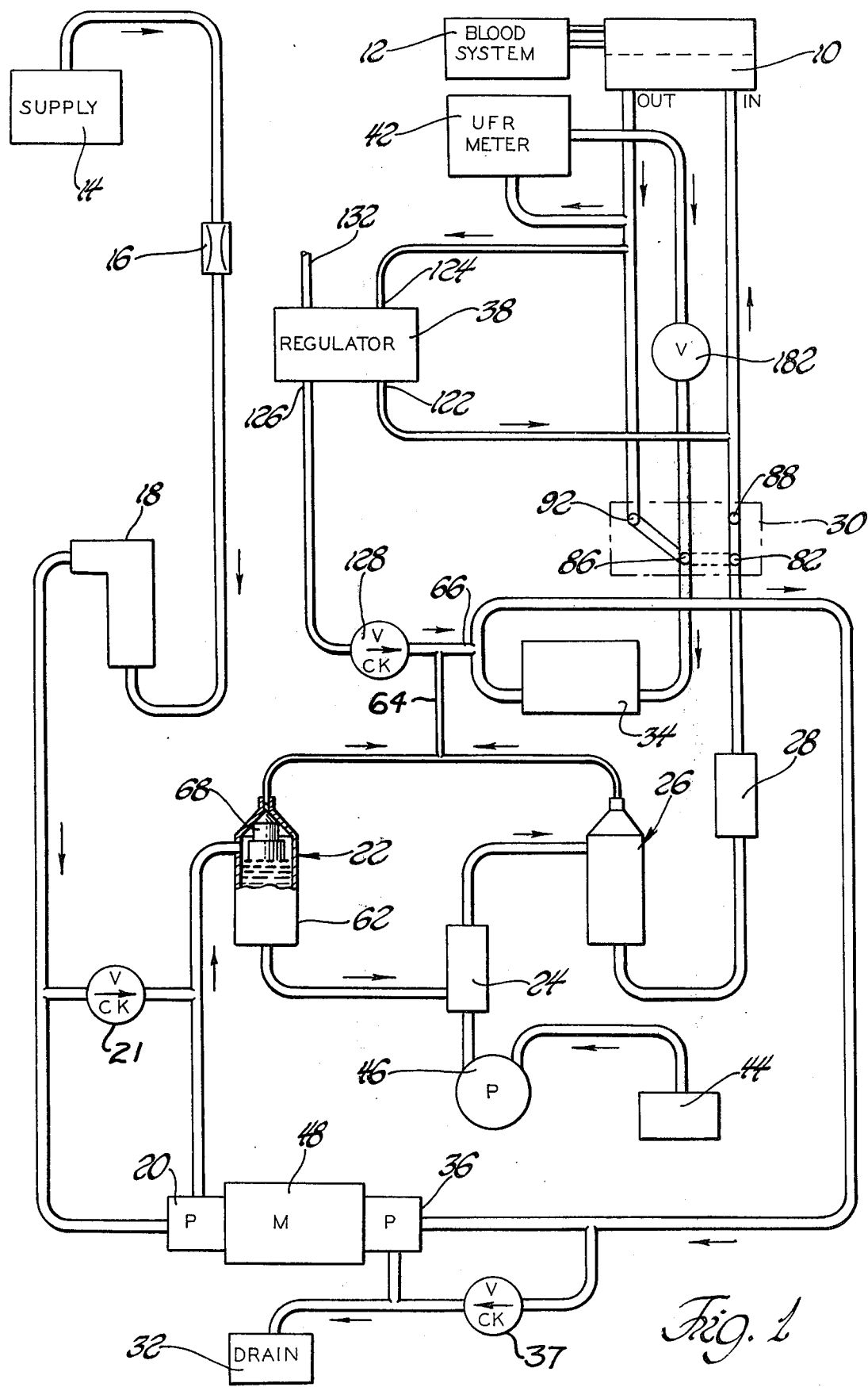
FIG. 1 is a diagram representing the dialysate control system of this invention.

An illustrative embodiment of the invention, as embodied in an artificial kidney, is shown in the drawings and will be described below with reference thereto.

In FIG. 1 the dialysate control system of this invention is shown in combination with a dialyzer 10 and a blood circulating system 12 which form part of the artificial kidney. The dialyzer and the blood circulating system, in practice, may take any one of several well known forms and the details thereof will not be described herein.

The dialysate flow control system comprises a water supply source 14 and a dialysate supply conduit extending therefrom and defining a flow path to the inlet of the dialyzer 10. The supply conduit, in general, includes a flow controller 16, a heater 18, a first stage suction pump 20, a first deaerator or air accumulator 22 and a mixer 24 for admitting a controlled quantity of concentrated dialysate solution to the dialysate flow path. The supply conduit additionally comprises a second accumulator 26, a conductivity monitoring cell 28 and a passage through a selector valve 30, which is connected to the inlet of the dialyzer 10. The dialysate flow control system also comprises an effluent conduit which defines a flow path extending from the outlet of the dialyzer 10 to a liquid drain 32. This effluent conduit includes a passage through the selector valve 30, a blood leak detector 34 and a second stage suction pump 36. The dialysate flow control system also comprises a negative pressure regulator 38. Additionally, an ultrafiltration rate meter 42 is included in the system. The pumps 20 and 36 have check valves 21 and 37 respectively, connected in parallel therewith to allow for liquid flow through the system when the pumps are not running. The dialysate flow control system will be described in greater detail below.

The water supply source 14 is suitably a tap of a municipal water supply and is pressurized, usually in the range of 20 to 50 psi. The supply water is also usually cooler than room temperature and will have a substantial quantity of air dissolved therein. The subject flow control system provides for heating the supply water to approximately body temperature, mixing the concentrated dialysate solution therewith and delivering the resulting dialysate to the dialyzer at a negative pressure; deaeration of the dialysate is provided to avoid the possibility of excessive air coming out of solution in the dialyzer due to the increase of temperature and decrease of pressure.

Figure 4:
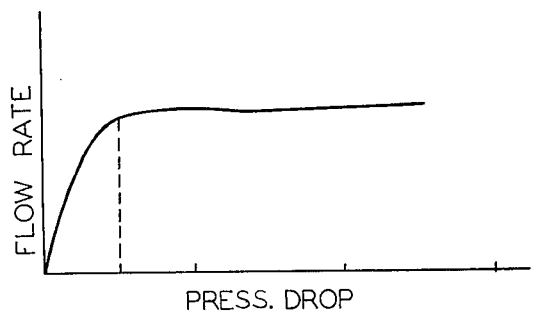
FIG. 4 is a graphical representation of the flow rate characteristic of the flow controller in the system of FIG. 1.
Figure 5:
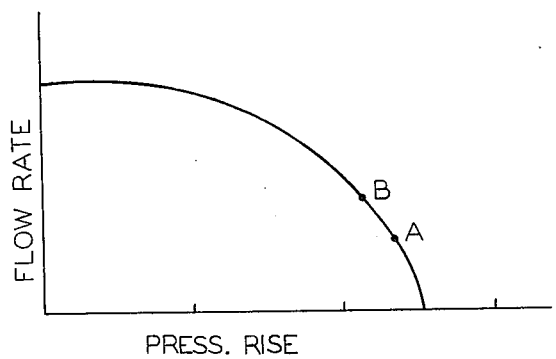
FIG. 5 is a graphical representation of the capacity characteristics of the pumps of the system of FIG. 1; and, FIG. 6 is a graphical representation of pressure variation in the dialysate flow path of the system of FIG. 1.

In order to develop the dialysate flow through the dialyzer at a negative pressure and to facilitate deaeration by negative pressure under all operating conditions, the system is provided with the flow controller 16, first stage suction pump 20 in the supply conduit, and the second stage suction pump 36 in the effluent conduit. The flow controller 16 is of conventional design and is essentially a flow restricting means which has a flow rate characteristic as illustrated in FIG. 4. It is noted that the quantity of liquid flow through the controller 16 increases nonlinearly with increasing pressure drop thereacross and reaches a substantially constant flow capacity at a predetermined pressure drop. For example, the flow controller may have a flow capacity of 425 milliliters per minute at 10 psi and remain substantially constant at higher values of pressure drop. The pump 20 which is driven by the motor 48 is a positive displacement pump which suitably exhibits a flow rate-pressure characteristic as represented by the graph in FIG. 5. The liquid displacement capacity decreases in a nonlinear fashion as the pressure rise across the pump (and hence, intake vacuum) increases. For example, the pump 20 may have a capacity of 1500 milliliters per minute when operating at zero head, i.e. with no pressure rise across the pump. The second stage pump 36 is also driven by the motor 48 and is the same type of pump with the same rated capacity as pumped 20. Hence, the pump 36 will have a characteristic the same as or nearly the same as illustrated in the graph of FIG. 5. For given operating conditions of the system, the pump 20 may be performing at operating point A on the curve of FIG. 5; i.e. a flow rate of 500 milliliters per minute at a pressure rise of 10 psi. However, pump 36 may be operated at a point B on the characteristic curve with a flow rate of 750 milliliters per minute at a pressure rise of 8 psi. The pressure of the dialysate in the dialyzer, and the operating condition of the pumps, is established by the setting of the negative pressure regulator 38, as will be further described below.

Figure 6:
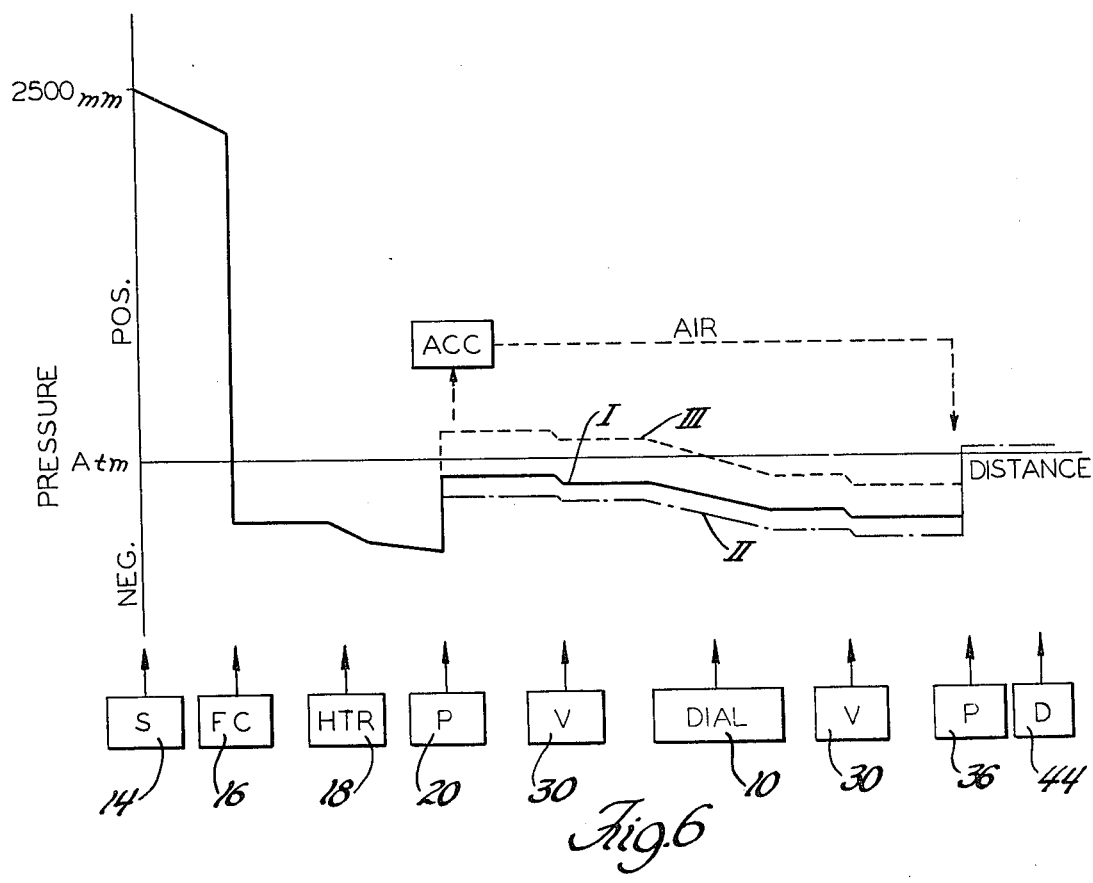

For explanatory purposes, a generalized graphical representation of pressure distribution in the dialysate flow control system is shown in FIG. 6. This graphical representation depicts pressure distribution between the water supply 20 and the drain 32, taking into account certain of the components of the system as identified in FIG. 6. In this Figure, the abscissa axis of the graph represents distance along the flow path and the ordinate axis represents pressure of the fluid in the flow path. It is noted that the intersection of the abscissa axis with the ordinate axis represents atmospheric pressure and that the curve extends from positive values of pressure to negative values of pressure, i.e. from above atmospheric to below atmospheric pressure values. The components in the flow path, as shown in FIG. 6, are arranged in the order in which they are encountered in the flow path in the downstream direction; the spacing of the components being arbitrary in FIG. 6, the relative positions and values being shown only for explanatory purposes.

The manner in which the negative pressure is produced in the flow control system will be described with reference to FIG. 1 and the pressure distribution curve of FIG. 6. The supply water from the source 14 is delivered at a positive pressure of several hundred torr. The pressure distribution as represented by the curve I in FIG. 6 is illustrative for a given operating condition of the flow control system with the pumps 20 and 36 in operation and the valve 30 in a so-called "run" position, i.e. selectively operated to cause the flow path to extend through the dialyzer 10. Thus, continuous liquid flow will be produced from the source 14, the high pressure upstream point as indicated in FIG. 6, to the drain 44, the low pressure downstream point. The flow controller 16 produces a large pressure drop at the point indicated on the curve I; in fact the pressure decreases from a high positive value to a relatively low negative value, i.e. below atmospheric. The negative pressure is produced by reason of the pump 20. (The Curve I in FIG. 6 shows pressure drops of linear character between components due to the flow resistance of the conduit. Certain components which are shown in FIG. 1, such as the blood leak detector 34, are not depicted in FIG. 6; further, a typical dialysate flow system may include the components in addition to those shown in FIG. 1, such as a water filter, pressure switch, and the like. While each component will produce some pressure drop in the flow path, the principles governing the negative pressure flow control system of this invention will remain the same.) The pump 20 reduces the pressure at the downstream side of the flow controller 16 to a negative value because the pump 20, as described above, is a positive displacement pump with a capacity greater than the flow rate which the flow controller can sustain at a pressure drop thereacross. In other words, the pump 20 is operating in a suction mode and the pressure between its inlet and the flow controller is below atmospheric. The pressure decreases somewhat in this flow interval due primarily to the flow resistance interposed by the heater 18. The pump 20, of course, produces a pressure rise between its inlet and outlet but, due to the action of the pump 36, the pressure does not rise above atmospheric, as shown by the curve I. The relatively small negative pressure at the outlet of pump 20 is maintained due to the action of the pump 36 which produces a flow rate which is adjustable by the controlled admission of air for pressure regulation in a manner to be described subsequently. Between the outlet of pump 20 and the inlet of the dialyzer 10, the flow path includes a portion of the selector valve 30 which causes a pressure drop as indicated. The flow path through the dialyzer 10 constitutes a resistance to flow and produces a linear pressure drop as indicated. From the outlet of the dialyzer pressure continues to decrease with a drop across another portion of the selector valve 30 and reaches the most negative value between the pumps at the inlet of pump 36. The pump 36 produces a pressure rise which is limited by the fluid pressure of the drain 44 encountered at the pump outlet. As indicated in FIG. 6, the drain pressure, and hence the discharge pressure of the pump 36, is just slightly above atmospheric pressure. The pressure distribution in the dialysate flow path will be discussed further below with reference to negative pressure regulation in the dialyzer; however, the foregoing discussion forms sufficient basis for description of the deaerating system of this invention.

Deaeration of the dialysate is accomplished in the flow path with the aid of negative pressure and dialysate heating at particular points in the flow path. The incoming supply water is typically in a condition such that it holds a relatively large quantity of dissolved air, i.e. the water is cool, well below room temperature, and the water is at a pressure of several hundred torr above atmospheric. In the supply conduit, between the flow controller 16 and the inlet of the first stage pump 20, the water pressure is reduced to a negative value, preferably a few hundred torr below atmospheric. The most negative pressure point in the dialysate flow system occurs at the inlet of the first stage pump 20. (This same value of negative pressure might be matched at the inlet of the effluent pump 36 under one extreme operating condition, which will be mentioned below.) The heater 18 is disposed in the flow path between the flow controller and the pump 20 and functions in a conventional manner to increase the temperature of the water to approximately the body temperature of the patient. Both the decrease in pressure and the increase in temperature tend to cause the dissolved air in the water to come out of solution in the form of minute bubbles entrained in the water. The combined temperature increase and pressure decrease is most effective in releasing the dissolved air since the water is supersaturated with air under such conditions. The release of the dissolved air is further enhanced by the fact that some of the water in contact with the heating element will attain temperatures well above the regulated value of the entire flow stream. Accordingly, the deaeration of the dialysate in the flow path occurs for the most part between the heater 18 and the pump 20. This deaeration process includes releasing of the dissolved air in the form of minute bubbles of air entrained in a liquid and the combining of the minute bubbles into larger bubbles which is a continuous process between the heater and the pump inlet. Thus the pump 20 pumps the liquid with the entrained air to a higher pressure through the first accumulator 22. This accumulator is shown diagrammatically in FIG. 1 and is shown in block form in FIG. 6 to indicate its position relative to the pressure distribution in the system. The accumulator 22 comprises a liquid container or a tank 62 with an inlet connection near the upper portion and an outlet connection at the lower portion. The tank 62 has a cross-sectional area substantially greater than that of the inlet and outlet conduits and hence the liquid is held for a time interval in the tank. While the liquid is standing in the tank 62 the air bubbles will tend to rise to the surface and accumulate above the surface of the liquid. The accumulator is provided with a vent or air outlet at its upper extremity, the outlet being connected through a discharge conduit 64 to an "air dump" point 66 downstream of the accumulator 62 and upstream of the second stage pump 36. The accumulator 22 is provided with a float valve 68 which is adapted to seat against a valve seat at the air outlet when the liquid in the tank raises above a predetermined level. When the liquid is below the predetermined level the vent is open and the accumulated air above the liquid will be vented through the conduit to the dump point 66.

The deaerated water from the accumulator 62 flows through the mixer which injects a relatively small volume of concentrated liquid dialysate into the stream of water. The mixer 24 is suitably of conventional construction and the "concentrate" is supplied thereto from the source 44 by the pump 46. The pump 46 is adapted to meter an accurately controlled volume of concentrate into the mixer and is suitably of the peristaltic type. Since this type of pump tends to produce a nonhomogeneous mixture of the concentrate and water, by reason of the periodic injections of concentrate, it is desirable to provide for additional mixing so that the concentration of the dialysate is uniform when it reaches the dialyzer. This is the principal purpose of the second accumulator 26; secondarily, this accumulator separates some additional quantity of air from the liquid dialysate. The accumulator 26 is suitably of the same construction as accumulator 22 and the air outlet is connected through the discharge conduit 64 to the air dump point 66. While the liquid dialysate stands in the tank of the accumulator 26 the mixture of concentrate and water becomes more uniform and any surging in the liquid flow due to the peristaltic pump pulsations is smoothed out prior to the dialyzer.

The liquid dialysate leaving the accumulator 26 is conditioned for entry into the dialyzer 10. The system is suitably provided with an automatic control loop for regulating the concentration of the dialysate and the temperature thereof. For this purpose, the monitor device 28 is interposed in the flow path and is adapted to produce an electrical signal indicative of conductivity of the dialysate for use in the concentrate control loop (not shown) which controls the pump 46. The monitor device 28 also includes a temperature sensor which produces an electrical signal indicative of dialysate temperature for the temperature control loop (not shown) which controls the heater 18. The control loops alluded to above may be of conventional design and are commonly used in artificial kidney machines. The location of the monitor device 28 after deaeration of the dialysate ensures that the conductivity measurement for concentration control will be unaffected by dissolved or entrained air in the liquid.

The selector valve 30 is adapted to switch the dialysate flow path so that it either extends through the dialyzer or so that it bypasses the dialyzer. The selector valve is shown schematically in FIG. 1 and with it in what is termed the "run" position, the passages depicted in solid lines are open while the passage depicted in dashed lines is closed, thus routing the flow path through a first passage in the valve to the inlet of the dialyzer 10 and from the outlet thereof back through a second passage in the valve 30. With the selector valve in what is termed the "bypass" position the first and second passages (shown in solid line) are closed and a third passage (shown in dashed lines) is open, thus routing the flow path around the dialyzer.

Figure 3:
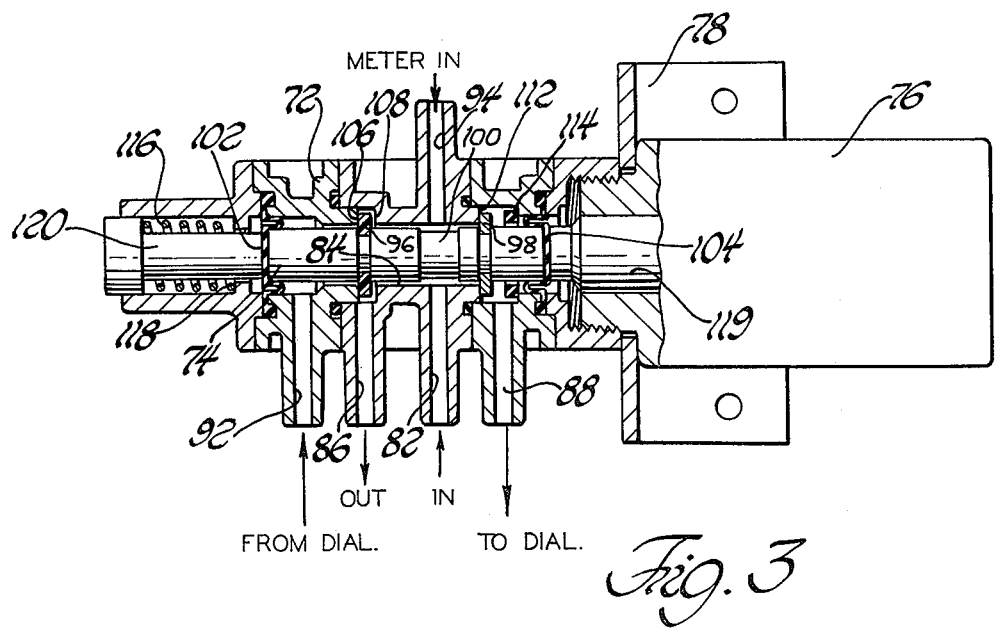
FIG. 3 shows the construction of a selector valve used in the system of FIG. 1.

Although the selector valve 30 may be of conventional design, a preferred valve structure is shown in FIG. 3; thus valve structure is especially advantageous for use in conjunction with the ultrafiltration rate meter 42, which will be described subsequently. As shown in FIG. 3, the selector valve 30 is a spool valve with an electromagnetic actuator. The valve comprises a valve body 72 which encloses a valve spool 74. The spool 74 is movable between first and second positions under the control of a solenoid 76 mounted on the valve body 72. The entire valve 30 is adapted to be supported on a panel by a mounting bracket 78. The valve body includes an inlet passage 82 adapted to be connected to the supply conduit and which extends to a central bore or chamber 84. The valve body also includes an outlet passage 86 extending from the central chamber 84 and adapted to be connected to the external conduit in the flow path through the blood leak detector 34 to the second stage pump 36. An outlet passage 88 extends through the valve body from the central chamber 84 and is adapted to be connected through an external conduit to the inlet of the dialyzer 10. Similarly, a return passage 92 extends from the central chamber 84 and is adapted to be connected to the outlet of the dialyzer 10. A metering passage 94 extends through the valve body from the central chamber 84 and is adapted to be connected to the outlet of the ultrafiltration rate meter 42.

The valve spool 74 comprises a cylindrical piston having a first valve land 96 and a second valve land 98 in axially spaced relation and having an intermediate waist 100 therebetween of reduced cross-section to increase the inlet area to the chamber 84. The valve spool 74 is supported for axial motion by a pair of seal members 102 and 104 disposed at opposite ends of the spool and suitably of the rolled diaphragm type. The seals 102 and 104 close the ends of the chamber 84 while allowing the spool 74 to move axially between a bypass position and a run position, such positions being described below. The valve body is provided with a pair of annular valve seats 106 and 108 which are disposed axially opposite each other and adapted to receive the valve land 96 therebetween in spaced relation. Similarly, the valve body is provided with a pair of annular valve seats 112 and 114 which are disposed axially opposite each other. The valve spool 74 is biased toward the bypass position and is illustrated in FIG. 3 in such position. A bias force is produced by a compression spring 116 which is seated on the shoulder 118 at the lefthand end of the valve body 72. The spring 116 reacts against the head of a movable plunger 120 which is guidably supported by a tubular extension at the lefthand end of the valve body 72. The plunger 120 is connected with the valve spool 74 through the intermediary of the diaphragm 102 so that the spool and plunger are movable in unison. In the bypass position of the valve spool 74, as shown in FIG. 3, the valve land 96 is in engagement with the annular valve seat 106 and the valve land 98 is in engagement with the annular valve seat 112. The valve spool 74 is actuated to the run position by the solenoid 76. The solenoid includes an armature 119 which is connected with the righthand end of the valve spool 74 through the intermediary of the diaphragm 104. Hence, the armature 119, valve spool 74, and plunger 120 are movable in unison. When the solenoid 76 is energized the armature 119 is retracted and the valve spool 74 is moved in the righthand direction against the resistance of the spring 116 until the valve lands 96 and 98 are in engagement with the annular valve seats 108 and 114, respectively.

When the selector valve 30 is in the bypass position, by reason of the solenoid 76 being deenergized, the flow path through the valve extends from the inlet passage 82 to the central chamber 84 and thence through the outlet passage 86; the meter passage 94 is also connected through the central chamber 84 to the outlet passage 86. When the selector valve is in the run position, by reason of energization of the solenoid 76, the valve spool 74 is moved in the righthand direction so that the valve lands 96 and 98 shut off the direct communication between the inlet passage 82 and the outlet passage 86 through the chamber 84. In the run position, the inlet passage 82 is connected through the chamber 84 to the outlet passage 88 which is connected with the inlet of the dialyzer. Also, in this position, the return passage 92, which is connected with the outlet of the dialyzer, is connected through the central chamber 84 to the outlet passage 86. Thus the dialyzer is included in the flow path of the dialysate.

According to this invention the pressure of the dialysate in the dialyzer is automatically regulated to maintain the predetermined value which is manually adjustable according to the needs of the individual patient. As illustrated in FIG. 1, the regulating means comprises a regulator 38 which is shown in block diagram with its interconnections with the dialysate flow path. The regulator is provided with a control liquid inlet 122 connected with a dialyzer inlet and is provided with a control liquid outlet 124 connected with a dialyzer outlet. Additionally, the regulator 38 is provided with a controlled fluid outlet 126 which is connected through a check valve 128 to the air dump point 66. The controlled fluid, preferably ambient air at atmospheric pressure, is supplied to the regulator 38 through a controlled fluid inlet 132.

Figure 2:
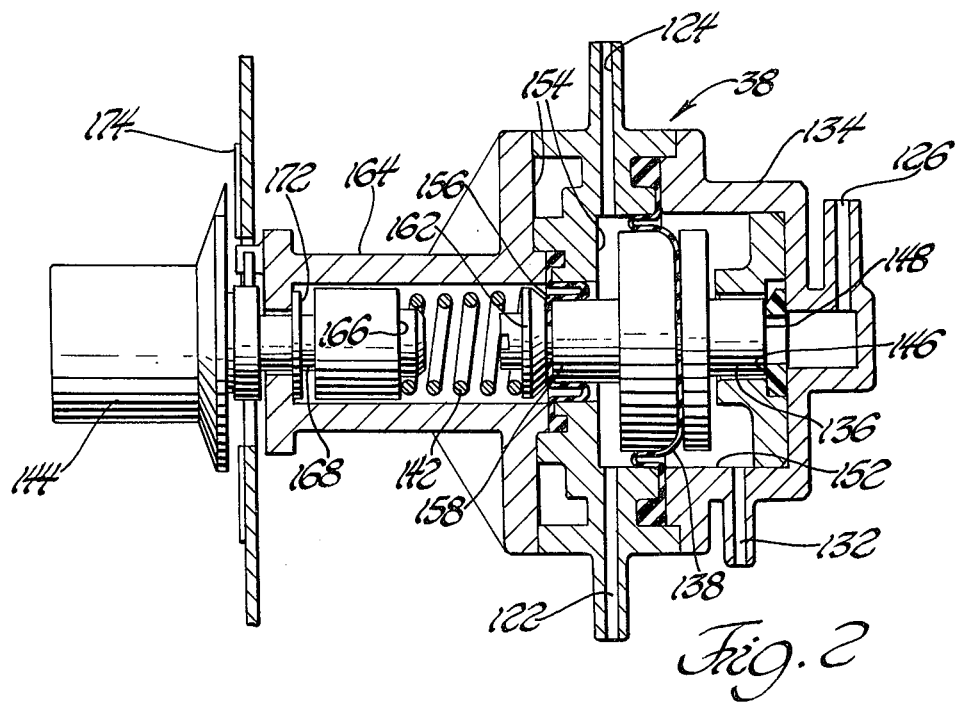
FIG. 2 shows the details of the pressure regulator employed in the system of FIG. 1.

The structure of the regulator 38 is shown in FIG. 2. The regulator comprises a regulator body 134 which defines the control liquid inlet 122 and outlet 124; it also defines the controlled fluid inlet 132 and outlet 126. The regulator body encloses a valve 136 which is mounted for axial movement by a diaphragm 138 to regulate the flow of the controlled fluid in accordance with the pressure of the control liquid. The valve 136 is biased in one direction by a compression spring which exerts a bias force which is adjustable by a manually actuable control knob 144.

In the regulator 38, the valve body 134 is provided with an annular valve seat 146 which is adapted to be engaged by the axial face 148 of the valve 136 to disconnect the air outlet 126 from the air inlet 132. When the valve 136 is retracted from the valve seat 146 the air outlet 126 is in fluid communication through a valve air chamber 152 with the air inlet 132. Within the valve body 134 a negative pressure chamber 154 is bounded at the righthand end by the diaphragm 138 and, at the lefthand end by a diaphragm 156, both diaphragms forming a fluid tight seal at their annular peripheries with the valve body. Within the negative pressure chamber 154 a piston 158 is supported for axial movement by the diaphragms 138 and 156. The valve 136 is mounted on the enlarged head of the piston 158 through the intermediary of the diaphragm 138 for movement therewith toward and away from the valve seat 146. The piston 158 is biased in the direction toward closure of the valve 136 against the valve seat 146 by the spring 142, which is seated at one end against a washer 162 mounted on the piston 158 through the intermdiary of the diaphragm 156. The spring 142 is disposed within a tubular body 164 and reacts against a traveling nut 166. The traveling nut is threadedly engaged by a lead screw 168 which is axially retained relative in the tubular body 164 by a snap ring 172 and rotatably mounted in a bearing portion of the body 164. The lead screw is manually rotatable by the knob 144 mounted thereon. The knob 144 is suitably provided with an index movable over a graduated scale plate 174 calibrated in units of pressure.

The regulator 38 is operative to regulate the pressure of the liquid in the negative pressure chamber 154 to a pressure value established by the bias force exerted by the spring 142 and, hence, the setting of the knob 144. The regulator functions in the manner of an adjustable relief valve except that it responds to negative pressure in the chamber 154 and when the negative pressure becomes excessively large, the force exerted by the piston 158 will exceed the bias force of the spring 142 with resulting leftward movement of the piston and the valve 136. This will displace the valve face 148 from the valve seat 146 and fluid will be admitted through the valve and external passages to relieve the suction in the negative pressure chamber 154. Thus the regulator 38 may be regarded as an adjustable suction relief valve. As shown in FIG. 1, with the control inlet 122 and the control outlet 124 connected to the dialyzer inlet and outlet respectively, the pressure in the negative pressure chamber 154 will be equal to the average value of pressure in the dialyzer 10, i.e. it will have a value midway between the inlet and outlet pressures of the dialyzer. The controlled fluid inlet 132 is in communication with the ambient air at atmospheric pressure, and, as previously noted, the controlled fluid outlet 126 is connected with the air dump point 66 through the check valve 128. When it is desired to operate the system with a small negative pressure in the dialyzer, the spring 142 is adjusted to exert a small bias force on the piston 158; when the regulated pressure in the dialyzer is to be a large negative value, the spring 142 is adjusted to exert a large force against the piston 158. The force of spring 142 is suitably adjustable by the knob 144 over a range corresponding to the pressure range extending from zero, i.e. atmospheric pressure, to 500 torr below atmospheric pressure.

Referring again to FIG. 6, the pressure distribution in the dialysate flow path as shown by curve I, which was previously described, represents a certain average negative pressure in the dialyzer, e.g. negative 350 torr. The average pressure in the dialyzer is maintained at the desired value by setting of the control knob 144 of the regulator 38 to produce a corresponding spring force. Since the pressure in the negative pressure chamber 154 is equal to the average pressure in the dialyzer, the regulator valve will remain closed so long as the average negative pressure in the dialyzer does not become greater than the set value. However, the second stage suction pump operates with the capacity which will continuously tend to increase the negative pressure to a value greater than the set value. When this excess value is reached the valve 136 is opened and admits air from the atmosphere through the control fluid inlet 132, the outlet 126 and the check valve 128 to the air dump point 66. A quantity of air is admitted to the intake of pump 36 sufficient to decrease the negative pressure in the dialyzer and hence in the pressure chamber 154 of the regulator to allow the valve 136 to close. This regulating action is repetitive during operation of the system, with the valve opening and closing occuring at a relatively high rate so that the pressure value oscillates or "hunts" about the regulated value through a very small range of deviation.

When it is desired to operate the dialyzer at a greater negative pressure, the regulator 38 is adjusted accordingly and the automatic regulation, as described above, will obtain. As shown in FIG. 6, operation of the dialyzer at different values of negative pressure results in different pressure distribution downstream of the first stage pump 20. The curve II represents the maximum value of negative pressure in the dialyzer and is obtained by setting the regulator with the maximum bias force on the spring 142; this bias force is effective to prevent the value 136 from opening at all, and hence no air is admitted through the regulator to the air dump point 66. The second stage suction pump 36 operates at its maximum suction which, produces about the same negative pressure at its inlet as the first stage suction pump 20 due to the substantially matched characteristics of the pump. The other extreme of dialyzer operating pressure is represented by curve III in FIG. 6 which depicts the average pressure in the dialyzer at zero or atmospheric value. This is achieved by setting the regulator so that the force of the bias spring 142 is at a minimum and approximately balanced by atmospheric pressure in the chamber 154. In this operating condition the dialysate is at a positive pressure at the inlet to dialyzer and is at a negative pressure at the outlet thereof, as shown by the curve III.

The pressure regulating system, as just described, is operative to respond to the dialyzer pressure during the run mode and also during the bypass mode of operation of the system. The selector valve 30, as described above, disconnects the inlet of the dialyzer from the dialysate flow path during the bypass mode of operation; it also disconnects the outlet of the dialyzer from direct connection with the flow path by disconnecting the return passage 92 from the outlet passage 86. However, the outlet of the dialyzer remains in fluid communication with the outlet passage 86 through the ultrafiltration rate meter 42, a check valve 182 and the meter passage 94. The outlet 124 of the regulator 38 is thereby connected through the ultrafiltration rate meter to the outlet passage 86 of the selector valve. Since this pressure value is communicated to the pressure chamber 154 in the regulator 38, the regulator will operate to change the dynamic pressure in the bypass until the pressure at the outlet passage 86 becomes equal to the average dynamic pressure in the dialyzer during the run mode. Accordingly, the ultrafiltration rate will remain the same in the bypass mode, and the volume of flow through the meter 42 and the outlet passage 86 will be due solely to the ultrafiltrate which permeates the dialyzer member. The ultrafiltration rate is therefore subject to accurate measurement by momentary switching of the selector valve 30 from run to bypass. The accuracy of this measurement is enhanced by reason of using the average dynamic pressure in the dialyzer as the control pressure in the regulator. This ensures that the dialysate flow through the meter occurs at the same pressure as the pressure in the dialyzer because, during the bypass mode, the regulator holds the pressure at outlet passage 86 at the same pressure as that in the dialyzer. If pressure other than the average value were to be sampled at the dialyzer for regulation purposes, there would be a change of pressure at the outlet passage 86 upon switching to bypass. This would change the ultrafiltration rate during bypass and therefore a reading representative of ultrafiltration rate during run would not be obtained. An ultrafiltration rate meter especially adapted for use with the subject invention is disclosed and claimed in copending patent application Ser. No. 520,337, filed on even date herewith by James T. Boag et. al. and assigned to the assignee of this application.

Although the description of this invention has been given with reference to a particular embodiment, it is not to be construed in a limiting sense. Many variations and modifications will now occur to those skilled in the art. For a definition of the invention reference is made to the appended claims.

The embodiments of the present invention in which an exclusive property or privilege is claimed are defined as follows:

1. In a dialysis machine, a negative pressure control system comprising a liquid conduit defining a flow path extending from a liquid source to a liquid drain, and adapted to include a dialyzer in said flow path, a flow controller in said flow path upstream of the dialyzer and constructed and arranged to restrict the flow rate through said conduit to a predetermined maximum value, a first positive displacement pump in said flow path between the flow controller and the dialyzer and having a pumping capacity exceeding said maximum value whereby a negative pressure is produced in the conduit between the flow controller and the first pump, a second positive displacement pump in said flow path between the dialyzer and the drain and having a pumping capacity exceeding that of said first pump whereby a negative pressure is produced in the conduit between the pumps and in the dialyzer, deaerating means in said flow path including a gas accumulator upstream of said dialyzer and a gas discharge conduit connected between the gas accumulator and the flow path downstream of said dialyzer, and negative pressure control means connected with the conduit between the pumps for regulating the negative pressure of the liquid in the dialyzer.

2. The invention as defined in claim 1 including regulating means having a control input adapted to be connected to the dialyzer and having a controlled output adapted to be connected between a source of fluid and said conduit downstream of said dialyzer, said regulating means being adapted to admit fluid to said conduit when the pressure in said dialyzer decreases below a predetermined value and thereby regulate the negative pressure at said dialyzer to said predetermined value.

3. The invention as defined in claim 2 including a mixer in said flow path upstream of said dialyzer and downstream of said flow restricting means, said mixer being connected with a source of concentrated dialysate solution, a second gas accumulator in said flow path between said flow restricting means and said mixer, and a concentration monitor device downstream of said second gas accumulator.

4. In a dialysis machine, a dialysate pressure control system comprising, a liquid conduit defining a flow path extending from a liquid source to a liquid drain and adapted to include a dialyzer in said flow path, flow producing means in said flow path for producing a negative pressure in the dialyzer, and regulating means including a valve member and a pressure actuated member, said pressure actuated member being in fluid communication with the inlet and the outlet of the dialyzer whereby the negative pressure upstream and downstream of the dialyzer is averaged and actuates the valve member between open and closed positions, conduit means for a source of regulating fluid, one side of the valve member being in fluid communication with the conduit means and the other side being in fluid communication with said conduit downstream of the dialyzer, said regulating means being constructed and arranged to admit regulating fluid to said conduit downstream of the dialyzer when the pressure in said dialyzer decreases below a predetermined value and thereby regulate the negative pressure at said dialyzer to said predetermined value.

5. The invention as defined in claim 4 wherein said regulating means further comprises pressure drop averaging means having an output connected with said pressure actuated member and having an input adapted to be connected with said dialyzer whereby said regulator is operative to regulate the average dynamic negative pressure in the dialyzer.

6. The invention as defined in claim 5 wherein said pressure averaging means comprises a conduit connected in parallel relation with said dialyzer and having a port at the midpoint thereof connected with said pressure actuated member.

7. The invention as defined in claim 5 including a flow rate meter having an inlet and an outlet, the meter inlet connected with the outlet of said dialyzer, valve means in said flow path for closing said flow path upstream of said dialyzer and downstream of said dialyzer whereby the regulated negative pressure is maintained in said dialyzer, said valve means including an auxiliary flow path for said liquid which bypasses said dialyzer, a connection between the meter outlet and said auxiliary flow path.

8. The invention as defined in claim 7 wherein said negative pressure producing means comprises a first pump downstream of said dialyzer, a flow restricting means in said flow path upstream of said dialyzer and a second pump in said flow path between said flow restricting means and said dialyzer.

9. The invention as defined in claim 8 wherein the fluid outlet of said regulating means is connected to said flow path between said dialyzer and said first pump.

10. The invention as defined in claim 9 including a gas accumulator upstream of said dialyzer and a gas discharge conduit connected between the gas accumulator and said flow path downstream of said dialyzer.

* * * * *